United States Patent
Bao et al.

(10) Patent No.: US 7,141,374 B2
(45) Date of Patent: Nov. 28, 2006

(54) TREATMENT OF SUBSTRATES FOR IMMOBILIZING BIOMOLECULES

(75) Inventors: Yijia Bao, Painted Post, NY (US); Guangshan Li, Corning, NY (US); Nalini Raghavachari, Painted Post, NY (US); Mingqian He, Painted Post, NY (US); Xinying Xie, Painted Post, NY (US); Yuming Xie, Painted Post, NY (US)

(73) Assignee: Corning Incorporated, Corning, NY (US)

(*) Notice: Subject to any disclaimer, the term of this patent is extended or adjusted under 35 U.S.C. 154(b) by 291 days.

(21) Appl. No.: 10/729,618

(22) Filed: Dec. 5, 2003

(65) Prior Publication Data

US 2004/0121391 A1    Jun. 24, 2004

Related U.S. Application Data

(62) Division of application No. 09/925,808, filed on Aug. 9, 2001, now Pat. No. 6,787,312.

(51) Int. Cl.
*C12Q 1/68* (2006.01)
*G01N 33/53* (2006.01)

(52) U.S. Cl. .......................................... 435/6; 435/7.1
(58) Field of Classification Search .................. 435/6; 536/23.1; 436/24.3
See application file for complete search history.

(56) References Cited

U.S. PATENT DOCUMENTS

| | | | |
|---|---|---|---|
| 5,807,522 A | 9/1998 | Brown et al. | |
| 6,110,426 A | 8/2000 | Shalon et al. | |
| 6,171,794 B1 | 1/2001 | Burchard et al. | ............. 435/6 |

FOREIGN PATENT DOCUMENTS

WO    WO2002033412    4/2002

OTHER PUBLICATIONS

"Super Microarray Substrates Handbook", www.arrayit.com, TeleChem International, Inc.

B. Clancy et al., "Reduction of Background Autofluorescence in Brain Sections Following Immersion in Sodium Borohydride", Journal of Neuroscience Methods, vol. 83 (1998), pp. 97-102.
W. Beisker et al., "An Improved Immunocytochemical Procedure for High-Sensitivity Detection of Incorporated Bromodeoxyuridine", Cytometry, vol. 8 (1987), pp. 235-239.
S.A. Schnell et al., "Reduction of Lipofuscin-like Autofluorescence in Fluorescently Labeled Tissue", Journal of Histochemistry and Cytochemistry, vol. 47, Jun. 1999, pp. 719-730.
M.C. Willingham, "An Alternative Fixation-Processing Method For Preembedding Ultrastructural Immunocytochemistry of Cytoplasmic Antigens: The GBS (glutaraldehyde-borohydride-saponin) Procedure", Journal of Histochemistry & Cytochemistry, vol. 31, Issue 6, Jun. 1, 1983, pp. 791-798.
M. Schena et al., "Parallel Human Genome Analysis: Microarray-Based Expression Monitoring of 1000 Genes", Proc. Natl. Acad. Sci. USA, vol. 93, Oct. 1996, Biochemistry, pp. 10614-10619.
N. Zammatteo et al., "Comparison Between Different Strategies of Covalent Attachment of DNA to Glass Surfaces to Build DNA Microarrays", Analytical Biochemistry, vol. 280, 2000, pp. 143-150.
F. Diehl et al., "Manufacturing DNA Microarrays of High Spot Homogeneity and Reduced Background Signal", Nucleic Acids Research, 2001, vol. 29, No. 7: E38, http://nar.oupjournals.org/cgi/content/full/29/7/c38.
Joon-Ik Ahn et al., Optimization of DNA Fabrication in Microarrays, Department of Biochemistry, College of Medicine & The Mental Health Institute, Hanyang University, Seoul.
Xenopore Binding Protocols, "Suggested Binding Protocols for Xenoslides", http://www.xenopore.com/binding.htm.
Reduction Reactions, "II Reduction Reactions", http://www.che.bharn.ac.uk/publicsite/staff/staff%20details/cox/teaching/reduction%20react . . .
"Sodium Borohydride Reduction", http://ice.chem.umbc.edu/Chem3521/borohydride.html.
Schena et al., PNAS, USA, 93 : 10,614-10,619 (Oct. 1996).

*Primary Examiner*—Ethan Whisenant
(74) *Attorney, Agent, or Firm*—Thomas R. Beall; Melissa K. Dobson

(57) ABSTRACT

A method of treating a substrate for immobilizing a biomolecule and substrates produced by the method are disclosed. The method includes contacting at least a portion of a substrate with a reducing agent such as a hydride. Treatment with an appropriate reducing agent substantially eliminates autofluorescence on substrates.

19 Claims, 6 Drawing Sheets
(5 of 6 Drawing Sheet(s) Filed in Color)

Before Pre-hyb     Post pre-hybe w/o NaBH4     Post pre-hybe w/ NaBH4

Autofluorescence reduction using NaBH4 on Human 6K array

FIG. 3A  FIG. 3B  FIG. 3C
Before Pre-hyb    Post pre-hybe w/o NaBH4    Post pre-hybe w/ NaBH4
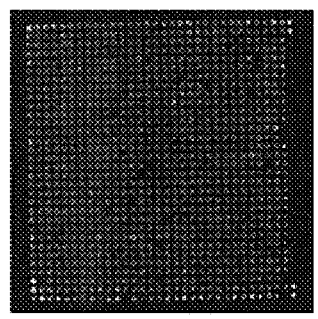 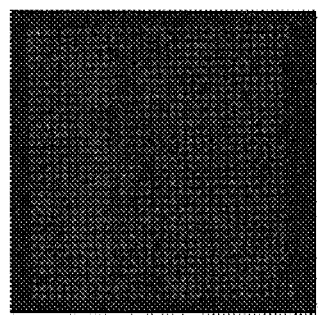 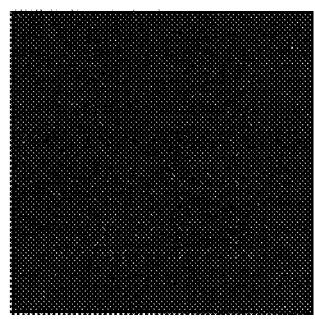
FIG. 4
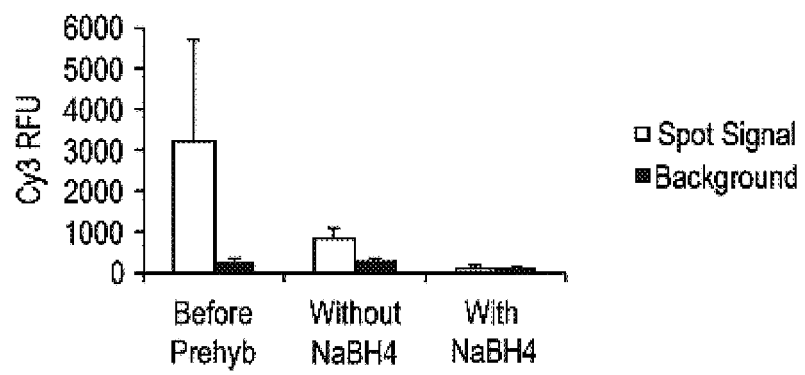

FIG. 5A
Without NaBH4 Treatment
FIG. 5B
With NaBH4 Treatment
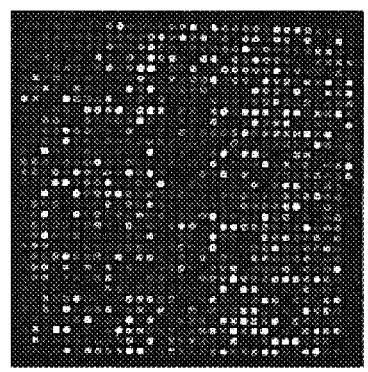
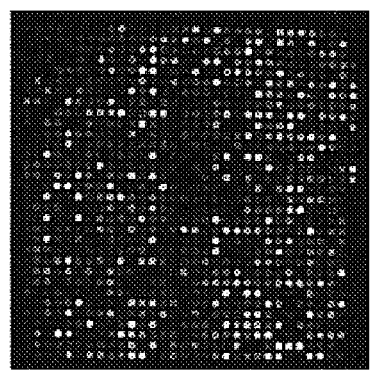
FIG. 6A
Self-self brain probe hybe on human 6k without NaBH4
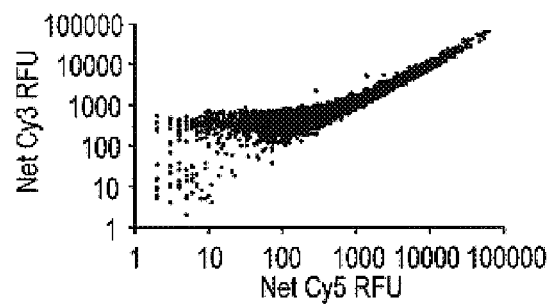
FIG. 6B
Self-self brain probe hybe on Human 6K with NaBH4 treatment
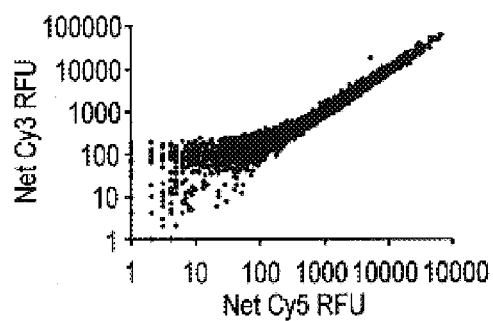

FIG. 7A
FIG. 7B
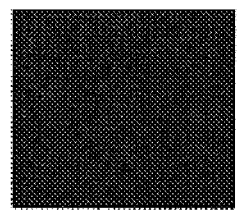
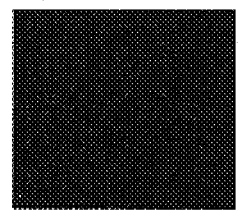
FIG. 7C
FIG. 7D
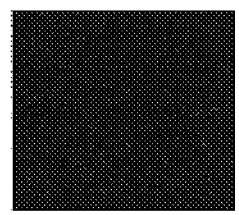
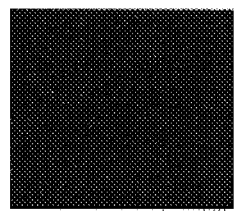
FIG. 8
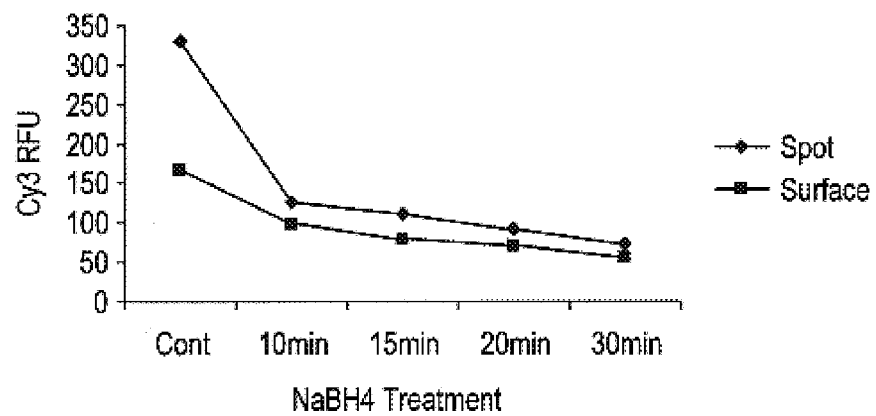

FIG. 9A  FIG. 9B  FIG. 9C
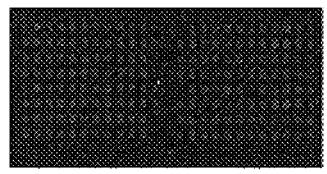 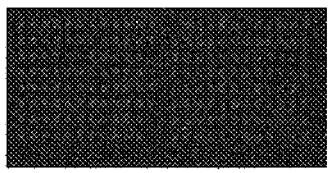 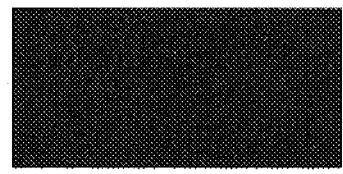
FIG. 10A  FIG. 10B
Before Pre-hyb
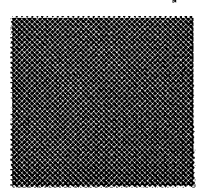
Post pre-hybe w/o NaBH4
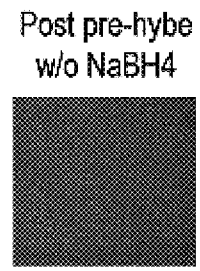
FIG. 10C  FIG. 10D
Post pre-hype w/ NaBH4
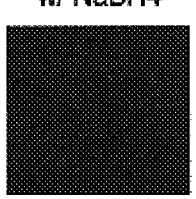
NaBH4 Treated GAPS Slide arraying and hybe
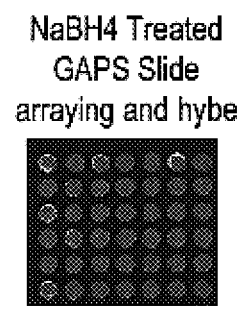

US 7,141,374 B2

TREATMENT OF SUBSTRATES FOR IMMOBILIZING BIOMOLECULES

This application is a division of application Ser. No. 09/925,808 filed Aug. 9, 2001 now U.S. Pat. No. 6,787,312, and the benefit of priority pursuant to 35 U.S.C. § 120 is hereby claimed.

FIELD OF THE INVENTION

This invention relates to substrates for use in immobilizing biomolecules and methods of making such substrates. More particularly, the present invention relates to treating substrates with a reducing agent and substrates produced by such treatment.

BACKGROUND OF THE INVENTION

Analysis of the structure, organization and sequence of nucleic acid molecules is important in the prediction, diagnosis and treatment of human disease and in the study of gene discovery, expression and development. One laboratory tool used in the analysis of nucleic acid molecules is the microarray or high density array (HDA), which is a microarray containing a large number of targets per square centimeter of array surface. The microarray provides the framework for immobilization of nucleic acid molecules for analysis on a rapid, large-scale basis. Microarrays generally include a substrate having a large number of positionally distinct nucleic acid targets attached to a surface of the substrate for subsequent hybridization to a nucleic acid target. The key to efficiently immobilizing nucleic acid molecules is the surface chemistry and the surface morphology of the microarrays substrate.

Microarrays have led to advances in biochemistry, chemistry and engineering that have enabled the development of a new gene expression assay. This "chip-based" approach utilizes microscopic arrays of cDNAs printed on glass substrates as high-density hybridization targets. Fluorescent target mixtures derived from total cellular messenger RNA (mRNA) hybridize to cognate elements on the array, allowing accurate measurement of the expression of the corresponding genes. A fundamental requirement for gene expression analysis using microarrays is a sensitive and robust method for detecting the hybridized sample to the target DNA immobilized on the array. When DNA microarrays are used to measure the relative expression of mRNA between two samples (e.g. experimental and control), the targets representing the two samples are each labeled with a different fluorescent dye, mixed and hybridized with the microarray. The ratio of the two dyes, which reflects the level of differential gene expression, is obtained by analyzing the array at the two different wavelengths. Therefore, to a large extent, the microarray performance depends on the optimal and accurate detection of fluorescence emitted by the fluorophores conjugated to the target molecules.

An important element for successful microarray expression analysis is the quality of the substrate onto which hybridization targets are spotted. Poor quality slides result in low nucleic acid binding efficiency, poor spot morphology and fluorescent background that is often both relatively high and non-uniform.

The surface of a substrate used for microarrays also must contain a suitable functional group for attaching target biomolecules such as DNA to the substrate surface. Target biomolecules such as DNA will not attach to a naked glass substrate. There are two general functionalities on glass substrates for attaching DNA to the substrate surface. One is a surface including an aldehyde functionality, which is used to covalently attach amino-modified DNA onto the surface by reaction with free aldehyde groups using Schiff's base chemistry. Another different type of functionalization of a substrate surface involves non-covalent attachment. Amine and lysine coated slides are two examples of many coatings that provide for non-covalent attachment of biomolecules such as DNA to the surface of a substrate. Another example of a coating that provides for noncovalent attachment of biomolecules is a silane coating, such as an amino propyl silane. One shortcoming of substrates including an aldehyde functional group is that the substrates typically must be rinsed with a reducing agent to reduce free aldehydes on the surface of the slide and prevent attachment of target biomolecules to locations on the substrate surface that do not contain biomolecules.

The surfaces of both organic and inorganic substrates can be modified by the deposition of a polymeric monolayer coating or film to construct biomolecular assemblies. In addition, surface modification can also be used to promote adhesion and lubrication, modify the electrical and optical properties of the substrate surface, and create electroactive films suitable for various optical and electronic sensors and devices.

As noted above, compounds with amine functionality have found extensive application in the preparation of surfaces for nucleic acid hybridization. Due to their ability to bond to a substrate with a hydroxide and their ability to bond to nucleic acids with an amine, silane compounds are useful as surface coatings that will effectively immobilize nucleic acids. One example of a silane used for biological assay preparation is gamma amino propyl silane (GAPS), which may be deposited by a variety of methods, including CVD, spin coating, spray coating and dip coating.

Fluorescence detection sensitivity is severely compromised by background signals, which may originate from endogenous sample constituents/surface to which the target is immobilized or from nonspecific hybridization of probes to the target. Generally, the nonspecific signals referred to as background, but not the intrinsic auto-fluorescence, can be eliminated by a high stringency wash of arrays after hybridization. The intrinsic auto-fluorescence of the arrays obscures the sensitivity of gene expression analysis to a large extent by hindering the detectability of the low-level specific fluorescent signals.

Attempts to diminish or eliminate auto-fluorescence by selecting filters that reduce the transmission of emission relative to excitation wavelength or by selecting filters that absorb and emit at longer wavelengths are partially successful, but still have limitations. Although narrowing the fluorescence detection bandwidth increases the resolution, it also compromises the overall fluorescence intensity detected.

While the present invention should not be limited by a particular theory of operation, it is believed that fluorescence is caused by an aptly conjugated electronic system in an organic molecule. There are multiple potential sources of auto-fluorescence. Auto-fluorescence could be due to trace impurities of fluorescent molecules that typically contain single or conjugated pi bonding. In addition, during storage or printing, adsorption and oxidation of some biological or chemical contaminants, could result in the emission of fluorescence.

With so many possible causative agents for autofluorescence, it appears that there are at least three possible ways to circumvent this major problem. A first way is to make an array without any contaminants. However, this is very difficult to achieve. A second way to eliminate autofluorescence is to wash out contaminants after arraying. A drawback of this approach is that this method may take long time and may end up either losing DNA targets partially or incomplete washing off the contaminants. A third way involves the use of relatively simple chemical means. Applicants have discovered a relatively rapid, reproducible and easily applicable method of substantially reducing autofluorescence on slides including a functional group for non-covalent attachment to a biomolecule.

Previous studies with reducing agents to eliminate autofluorescence from paraffin embedded tissue sections were found to significantly decrease deceptive false positive fluorescent signals. Hydrides are known to reduce the conjugated system in organic molecules. Sodium borohydride and sodium cyanoborohydride are mild reagents and hydride donors, which are known to reduce double bonds in conjugated systems. They both work well to reduce background signals in tissue section for histochemistry and cytochemistry studies. See, e.g., Schnell, S A, Staines, S A and Wessendorf, M W. J., Reduction of lipofuschin like auto-fluorescence in fluorescently labeled tissue, Histochemistry Cytochemistry, 1999. 47 (6), 719–30; Clancy, B and Cauller, L. J. J., Reduction of background auto-fluorescence in brain sections following immersion in sodium borohydride, Neuroscience Methods, 83, 1998. 97–102; Beisker, W Dolberate, F. and Gray J W, An improved immunocytochemical procedure for high sensitivity detection of incorporated bromodeoxyuridine, Cytometry 1987: 8: 235–9; and Willingham M C. J. Histochemistry Cytochemistry, Alternative fixation processing method for preembedding ultrastructural immunocytochemistry of cytoplasmic antigens, 1983: 31–791–889.

Taking into account the wide variety of factors contributing to autofluorescence, techniques for the elimination of autofluorescence in one biological system containing a specific type of organic molecules and chemicals would not be expected work in a system employing different organic molecules and chemicals. Furthermore, methods used in the elimination of autofluorescence problems in bulk tissue samples would not be expected to be useful in the elimination of autofluorescense on substrates used for microarrays. Other researchers have suggested eliminating autofluorescense on slides containing non-covalent attachment functionality through curing by baking at high temperatures. See, e.g., Super Microarray Substrates Handbook, Telechem International, Inc.//arrayit.com, www.arrayit.com, 1999. However, applicants experiments have found that curing of the slides in an oven was largely ineffective in reducing auto-fluorescence.

It would be useful to provide an improved method of treating substrates for immobilization and hybridization of biomolecules such as nucleic acids and oligonucleotides. The method should have the ability to be performed in a reproducible manner. It would also be advantageous to provide a substrate that has uniform surface characteristics and exhibits low background noise or autofluorescence when the substrate is analyzed using fluorescence scanning.

SUMMARY OF INVENTION

Accordingly, the present invention generally provides a method of immobilizing biomolecules on a surface of a substrate that provides reduced levels of autofluorescence on the substrate. The method includes providing a substrate having a first surface including a functional group for non-covalent attachment to a biomolecule and contacting at least a portion of the first surface with a reducing agent. The method further includes attaching a biomolecule to the functional group. According to one aspect of the invention, the reducing agent is selected from the group consisting of hydrides. Applicants have surprisingly discovered that treatment with a reducing agent such as a hydride significantly diminishes autofluorescence on the surface of the substrate as well as on the locations deposited on the substrate. In a preferred aspect of the invention, the reducing agent includes a borohydride, and more preferably, sodium borohydride. According to a most preferred aspect of the invention, the sodium borohydride is in a solution at a concentration ranging from 0.01% to 1% weight per unit volume. Other potential reducing agents that may be used in accordance with the invention include sodium cyanoborohydride and copper sulfate.

Another aspect of the invention relates to a method of reducing autofluorescence on substrate containing an array of biomolecules. According to this aspect of the invention, the method includes providing a substrate having an array of target biomolecules non-covalently attached to at least a first surface of the substrate, treating at least a portion of the first surface of the substrate with a reducing agent, and hybridizing complementary biomolecules to the target biomolecules. After hybridization, the substrate is scanned. Preferably, the complementary target biomolecules contain a fluorescent label, and the step of scanning the substrate includes scanning the substrate for the fluorescent label.

According to a preferred aspect of the invention, the solution for treating the substrate includes a hydride, and more preferably, a borohydride. Most preferably, the step of treating the substrate with a reducing agent includes contacting at least a portion of the first surface of the substrate with an aqueous solution containing between 0.1 and 1% sodium borohydride by volume. Another aspect of the invention relates to having an array of biomolecules non-covalently attached thereto produced by the methods described above.

According to one aspect of the invention, the immobilized biomolecules are nucleic acid molecules or oligonucleotides. In a preferred aspect of the invention, the substrate is a high density array or microarray.

The present invention provides a simplified and reproducible method of providing substrates for immobilizing biomolecules. Experimentation has indicated that the substrates produced according to the invention have good stability, reproducibility and exhibit low background noise. Additional features and advantages of the invention will be set forth in the following description. It is to be understood that both the foregoing general description and the following detailed description are exemplary and are intended to provide further explanation of the invention as claimed.

BRIEF DESCRIPTION OF THE DRAWINGS

This application file contains at least one drawing executed in color. Copies of this patent application publication with color drawing(s) will be provided by Applicant upon request and payment of the necessary fee.

FIG. 3A shows a representative Cy3 image of a slide before washing with any solution under a PMT setting of 800 volts;

FIG. 3B shows a representative Cy3 image of a slide washed without a reducing agent under a PMT setting of 800 volts;

FIG. 3C shows a representative Cy3 image of a slide washed with a reducing agent under a PMT setting of 800 volts;

FIG. 4 is a bar graph comparing the Cy3 RFU readings for the untreated slide, the slide washed without reducing agent and the slide treated with sodium borohydride;

FIG. 5A shows a representative post-hybridization image of a slide printed with washed without reducing agent;

FIG. 5B shows a representative post-hybridization image of a slide washed and treated with sodium borohydride;

FIG. 6A is a graph of net Cy3 RFU versus net Cy5 RFU for the slide without sodium borohydride treatment;

FIG. 6B is a graph of net Cy3 RFU versus net Cy5 RFU for the slide with sodium borohydride treatment;

FIG. 7A shows a representative Cy3 image of a slide washed without reducing agent;

FIG. 7B shows a representative Cy3 image of slide washed with reducing agent sodium borohydride for 10 minutes;

FIG. 7C shows a representative Cy3 image of slide washed with reducing agent sodium borohydride for 20 minutes;

FIG. 7D shows a representative Cy3 image of slide washed with reducing agent sodium borohydride for 30 minutes;

FIG. 8 is a graph comparing the spot and surface fluorescence of each of the samples in FIGS. 7A–7D;

FIG. 9A is a representative Cy3 image of a subgrid of an array of oligonucleotides without washing;

FIG. 9B shows a representative Cy3 image of a subgrid of an array of oligonucleotides using wash procedures without sodium borohydride;

FIG. 9C shows a representative Cy3 image of a subgrid of an array of oligonucleotides using wash procedures with sodium borohydride;

FIG. 10A shows a representative Cy3 image of a slide before treatment not treatment obtained at a PMT setting of 950 volts;

FIG. 10B shows a representative Cy3 image of a slide washed according to procedures described above without sodium borohydride obtained at a PMT setting of 950 volts;

FIG. 10C shows a representative Cy3 image of a slide washed according to procedures described above with sodium borohydride obtained at a PMT setting of 950 volts;

FIG. 10D shows a representative Cy3 image of a slide washed according to procedures described above with sodium borohydride and after arraying and hybridization obtained at a PMT setting of 950 volts;

DETAILED DESCRIPTION

Figures 1A, 1B, 1C:
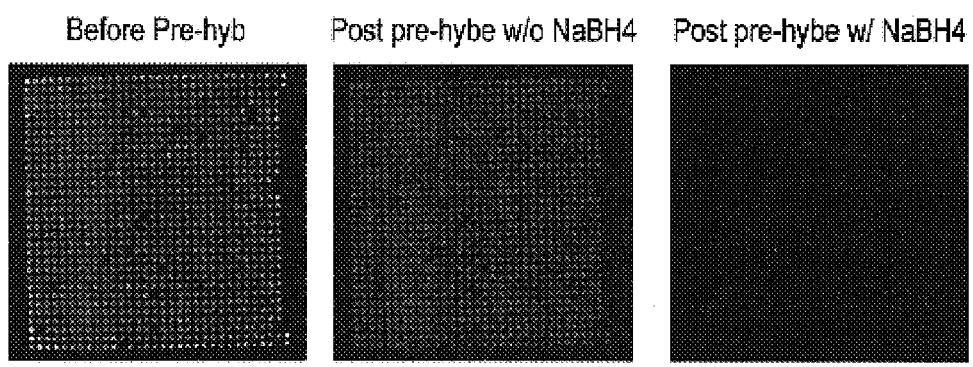
FIG. 1A shows a representative Cy3 image of a slide before washing with any solution under a PMT setting of 950 volts.
FIG. 1B show a representative Cy3 image of a slide washed without a reducing agent under a PMT setting of 950 volts.
FIG. 1C shows a representative Cy3 image of a slide washed with a reducing agent under a PMT setting of 950 volts.

Reference will now be made in detail to the present preferred embodiment of the invention. The invention provides a method of treating substrates for immobilization of a biomolecule and substrates produced by the method having a biomolecule immobilized thereon. Applicants have surprisingly discovered that autofluorescence on the slide surface including a functional group for non-covalent attachment to a biomolecule as well as on target biomolecules can be substantially reduced by treating the surface of the slide with a reducing agent as described further below.

According to the present invention, biomolecules are immobilized on a surface of a substrate having a first surface including a functional group for non-covalent attachment to a biomolecule. When the substrate used for immobilizing biomolecules is a glass substrate, it is preferred that hydroxy functional groups are present. Amine moieties are also preferably present to provide interaction with DNA and other biomolecules. Particularly preferred substrates include a surface coated with an amino propyl silane, such as gamma amino propyl silane.

Suitable substrates for this invention are those having a surface that is accessible to solvents. The substrate itself may take any shape including, but not limited to, rectangular, square, circular, cylindrical, conical, planar and spherical. The interior surface of a bottle or tubing could be used as a substrate. The preferred substrate has a planar shape, and may be formed into a variety of microarrays, HDAs, microplates and laboratory dishes.

For optical or electrical areas of application, the substrate can be transparent, impermeable or reflecting, as well as electrically conducting, semiconducting or insulating. For biological applications, the substrate material may be either porous or nonporous and may be selected from either organic or inorganic materials.

Inorganic substrate materials can include metals, semiconductor materials, glass and ceramic materials. Examples of metals that can be used as substrate materials are gold, platinum, nickel, palladium, aluminum, chromium, steel and gallium arsenide. Semiconductor materials used for the substrate material can include silicon and germanium. Glass and ceramic materials used for the substrate material can include quartz, glass, porcelain, alkaline earth aluminoborosilicate glass and other mixed oxides. Further examples of inorganic substrate materials include graphite, zinc selenide, mica, silica, lithium niobate, and inorganic single crystal materials.

Organic substrate materials are typically made from polymer materials, due to their dimensional stability and resistance to solvents. Examples of organic substrate materials are polyesters, such as polyethylene terephthalate, and polybutylene terephthalate, polyvinylchloride, polyvinylidene fluoride, polytetrafluoroethylene, polycarbonate, polyamide, poly(meth)acrylate, polystyrene, polyethylene or ethylene/vinyl acetate copolymer.

According to one embodiment of the invention, DNA or oligonucleotides are attached to a substrate having a coating or a layer including a functional group for non-covalent attachment to a biomolecule. Other biological or synthetic molecules can be attached to the coated substrate. For example, other synthetic molecules include, but are not limited to, ribonucleic acids (RNA), deoxyribonucleic acids (DNA), synthetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates, and haptens.

To facilitate non-covalent attachment of biomolecules, it is desirable for the coating or layer on the substrate to include one of various functional groups. These functional groups may include, but are not limited to, primary amines, propyl hydrocarbon chain segments, silanol groups and siloxane bonds. Although the invention should not be limited to a particular theory of operation, generally, immobilization of molecules at a substrate surface occurs in two steps: attraction of the molecules to the surface and binding of the molecules to the surface. Some or all of the functional groups exposed on the surface of the silsesquioxane coating may contribute the attraction and binding of biomolecules or biomaterials, resulting in their immobilization on the substrate. For example, a protonated primary amine is positively charged and may charge-attract and bind biomolecules. Propyl hydrocarbon chains are hydrophobic, and their hydrophobic interaction with hydrophobic segments of biomolecules may assist in binding them to the surface. Other interactions between biomolecules and coated substrates are, of course, possible and the above discussion is not intended to be exhaustive or limiting of the mechanisms, which may play a role in the immobilization of biomolecules on coated substrates in accordance with this invention.

According to method aspects of the present invention, a substrate including a coating to promote non-covalent attachment of biomolecules is provided and treated with a reducing agent. As discussed above, variability in spot size and high background levels can be problematic in biomolecule hybridization and scanning for hybridization. Variability in spot size and high background levels can arise from non-uniformities in a slide's coating which, in turn, can result in a working surface whose hydrophilic/hydrophobic properties are non-uniform.

Various techniques are known in the art for immobilizing DNA and oligonucleotides on surfaces, essentially any of which can be used in the practice of the invention. A discussion of representative immobilization techniques used in the art can be found in U.S. Pat. No. 5,919,626 and the references listed in that patent. Similarly, immobilization techniques are known for other biomolecules, such as specific binding members. Along the same lines, techniques for immobilization of molecules useful in tissue culture systems, e.g., collagen, are also well-known in the art. It is understood that surfaces produced in accordance with the present invention can be used to immobilize a variety of biomolecules including, but not limited to DNA arrays, oligonucleotides, protein arrays, antibody arrays, peptide arrays and cell arrays.

EXAMPLES

Example 1

Cleaning of Slides

Corning Microarray Technologies (CMT™) GAPS™ coated slides, which are 25×75 mm glass slides coated with an amino-silane surface chemistry that enables the even immobilization of DNA were first cleaned as follows. Three different groups of slides were generally provided. A first set of slides was used as received. A second set of slides was cleaned as follows:
1. Freshly made pre-hybridization solution was prepared containing: 2×SSC/0.05% SDS/0.2% BSA.
2. 100 ml of pre-hybridization solution was added into a Coplin jar and the solution was warmed up to 42° C. in a water bath (for about 20–30 min), and the slides were soaked (maximum of 4 slides/jar) for 10 min, at 42° C.
3. The slides were then transferred to Coplin jar filled with 1×SSC at RT for 2 minutes.
4. There slides were transferred to Coplin jar filled with 0.2×SSC at RT for 2 min.
5. Step 4 was repeated twice.
6. Slides were dried by spinning at 2000 rpm, 2 min, 25° C.

A third set of slides was cleaned and treated with reducing agent as follows:
1. Freshly made pre-hybridization solution was prepared containing: 2×SSC/0.05% SDS/0.2% BSA.
2. 100 ml of pre-hybridization solution was added into a Coplin jar and the solution was warmed up to 42° C. in a water bath (for about 20–30 min), and the slides were soaked (maximum of 4 slides/jar) for 10 min, at 42° C.
3. The slides were transferred to Coplin jar filled with 2×SSC/0.05% SDS/0.25% $NaBH_4$ at 42° C. for 15 min.
4. The slides were then transferred to Coplin jar filled with 1×SSC at RT for 2 minutes.
5. There slides were transferred to Coplin jar filled with 0.2×SSC at RT for 2 min.
6. Step 5 was repeated twice.
7. Slides were dried by spinning at 2000 rpm, 2 min, 25° C.

Printing and Hybridization

Printing the DNA targets was performed on the CMT-GAPS slides available from Corning, Inc. using conventional procedures. It will be understood that reduction in autofluorescence according to the present invention does not depend on the type of printing technique. Accordingly, either contact printing or ink-jetting technologies can be used to print microarrays. Targets were prepared by labeling RNA with reverse transcriptase and Cy3 and/or Cy5.

In Examples in which hybridization was performed, each array was hybridized with a solution consisting of 29% formamide, 2.25×SSC, 6% dextran sulfate, 0.17 µg/µL poly A, 0.10 µg/µL Cot 1 DNA, 0.2% BSA, and a given amount of labeled cDNA. For hybridization, 60 µL of this solution was spotted onto the array and then spread over the entire surface using a 24 mm×60 mm coverslip (Lifterslip, Erie Scientific Company). The arrays were incubated overnight at 42° C.

In Examples in which hybridization was performed, slides were washed after hybridization according to the following procedures:
1. Slides were soaked in 2×SSC, 0.05% SDS at 42° C. and the coverslip was removed. The slides were transferred to a coplin jar containing 2×SSC, 0.05% SDS at 42° C. for 5 min. This washing procedure was repeated twice.
2. Slides were transferred to a coplin jar containing 1×SSC at RT for 5 min. This washing procedure was repeated twice.
3. Slides were transferred to a coplin jar containing 0.2×SSC, at RT for 2 min. This washing procedure was repeated thrice.
4. Slides were spin dried.

Imaging

A GenePix 4000A (Axon Instruments) fluorescence scanner was used to obtain the Cy3/Cy5 fluorescence images using a PMT setting of 750–950 volts. All images were analyzed using GenePix Pro 3.0 analysis software (Axon Instruments).

Example 1

Figure 2:
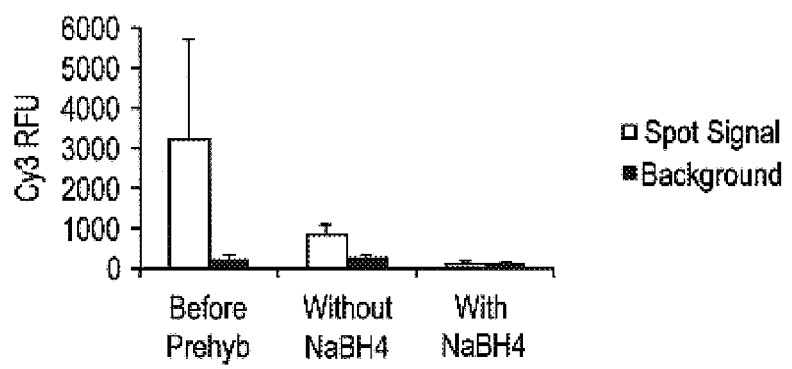
FIG. 2 is a bar graph depicting the reduction in background fluorescence produced by washing slides with a reducing agent.

FIGS. 1A–1C show representative Cy3 images of a 1000 gene sub-grid of a microarrays of 2000 cDNA human DNA clones printed on CMT GAPS™ slides before and after treatment with 0.25% sodium borohydride, under a PMT setting of 950 volts. Referring to FIG. 1A which is an image of a slide before washing with any solution, both positive and negative spots are observed, indicating that the target quality is inconsistent since the spot fluorescent intensity either higher or lower than the background intensity on the GAPS surface. Analysis of the images showed that the normal prewash couldn't get rid of autofluorescence on both spots and the surface. FIG. 1B shows an image of a slide washed according to the procedures described above without sodium borohydride. Analysis of the images in FIG. 2B showed that the prewash without reducing agent could not reduce autofluorescence on both spots and the surface. FIG. 1C shows an image of a slide treated according to the procedures above with sodium borohydride. As FIG. 1C shows, treatment with sodium borohydride significantly reduces auto-fluorescence of both surface and spots on Human 2K array. FIG. 2 shows that the slides treated with sodium borohydride reduced the relative fluorescence unit reading from the slides was reduced from approximately 1500 to less than 500 when compared with an untreated slide and a slide treated without reducing agent.

Example 2

FIGS. 3A–C show representative Cy3 images of a 1000 gene sub-grid of an array of microarrays of 6000 cDNA human DNA clones printed on a CMT GAPS™ slides before and after treatment with 0.25% sodium borohydride, under a PMT setting of 800 volts. FIG. 3A is an image of an untreated slide. FIG. 3B is an image of a slide washed without treatment with reducing agent. FIG. 3C is an image of a slide washed and treated with sodium borohydride. FIG. 4 is a bar graph comparing the Cy3 RFU readings for the untreated slide, the slide washed without reducing agent and the slide treated with sodium borohydride. As shown in FIGS. 3A–C and FIG. 4, treatment significantly reduces auto-fluorescence on the microarray. Analysis of the image in FIG. 2B shows that even though a conventional pre-wash can remove auto-fluorescence on target spots partially, it can not remove autofluorescence on the surface at all. However, as can be seen from FIG. 2C, when treated with reducing agent, the autofluorescence from both the spots and the surface is substantially eliminated.

Example 3

To test if reducing agent treatment affects the target hybridization, self-self hybridization of microarrays of 6000 cDNA human DNA cancer clones printed on a CMT GAPS™ slides (treated and untreated with sodium borohydride) with 0.25 µg of total human brain RNA through linear amplification and reverse transcription labeling was also performed. FIG. 5A is an image a slide washed without reducing agent, and FIG. 5B is an image of a slide washed and treated with sodium borohydride according to the procedures described above. FIG. 6A is a graph of net Cy3 RFU versus net Cy5 RFU for the slide without sodium borohydride treatment and FIG. 6B is a graph of net Cy3 RFU versus net Cy5 RFU for the slide with sodium borohydride treatment. FIG. 6A shows more genes have higher Cy3/Cy5 between 100–1000 on the untreated slides due to the Cy3 autofluorescence, when compared with the graph in FIG. 6B. This suggests that without sodium borohydride treatment, the Cy3 auto-fluorescence significantly affected the signal ratio in comparison to slides treated with 0.25% sodium borohydride. This ultimately led to improvement in gene expression profile.

Example 4

The time course of the reduction process has also been tested. Representative Cy3 images of a 1000 gene subgrid of microarrays of 4000 cDNA human DNA cancer clones printed on a CMT GAPS™ slides before and after treatment with 0.25% sodium borohydride, under a PMT setting of 800 volts are shown in FIGS. 7A–7D. FIG. 7A is a representative Cy3 image of a slide washed without reducing agent. FIG. 7B is a representative Cy3 image of slide washed with reducing agent according to procedures described above with sodium borohydride for 10 minutes. FIG. 7C is a representative Cy3 image of slide washed with reducing agent according to procedures described above with sodium borohydride for 20 minutes. FIG. 7D is a representative Cy3 image of slide washed with reducing agent according to procedures described above with sodium borohydride for 30 minutes. FIG. 8 is a graph comparing the spot and surface fluorescence of each of the samples. As shown in FIGS. 7A–7D and FIG. 8, when the reduction process with sodium borohydride was extended from 10 minutes to 30 min, greater elimination of auto-fluorescence was achieved.

Example 5

In addition to above cDNA arrays, oligonucleotide array performance on CMT GAPS™ slides has also been evaluated. FIG. 9A is a representative Cy3 image of a subgrid of an array of oligonucleotides without washing. FIG. 9B is a representative Cy3 image of a subgrid of an array of oligonucleotides using wash procedures without sodium borohydride as described above. FIG. 9C is a representative Cy3 image of a subgrid of an array of oligonucleotides using wash procedures with sodium borohydride as described above. The representative Cy3 images in FIGS. 9A–9C were obtained under a PMT setting of 800 volts. Once again, NaBH4 treatment significantly reduces oligonucleotide array auto-fluorescence, for both targets and GAPS surface itself.

Hybridization of liver and bacterial on oligonucleotide arrays printed on CMT GAPS™ slides also showed improved signal/noise ratio after treatment with sodium borohydride in comparison to the untreated arrays (not shown). Image analysis revealed that higher signal-to-background ratio was obtained on the treated slides mostly due to the reduced background intensity.

Example 6

Figure 11A:
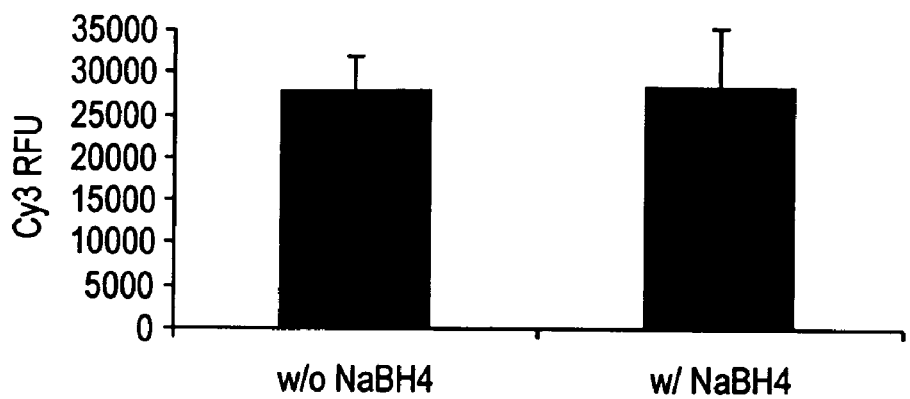
FIG. 11A is a graph comparing Cy3 RFU readings prior to hybridization for unwashed slides, slides washed without reducing agent and slides washed with reducing agent.
Figure 11B:
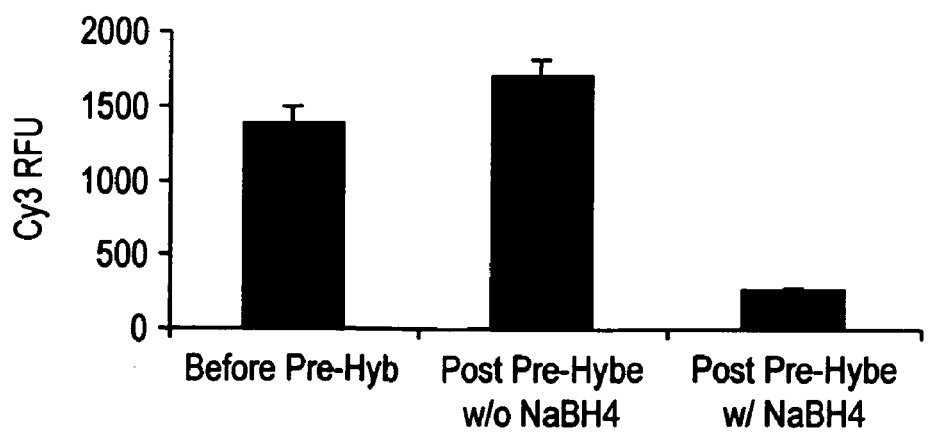
FIG. 11B is a graph showing Cy3 reading on slides washed without reducing agent and slides washed with reducing agent after hybridization.

Experiments were performed to determine the effect of pre-treatment of CMT GAPS™ slides prior to printing of targets and hybridization. FIG. 10A shows a representative Cy3 image of a slide before treatment not treatment obtained at a PMT setting of 950 volts. FIG. 10B shows a representative Cy3 image of a slide washed according to procedures described above without sodium borohydride obtained at a PMT setting of 950 volts. FIG. 10C shows a representative Cy3 image of a slide washed according to procedures described above with sodium borohydride obtained at a PMT setting of 950 volts. FIG. 10D shows a representative Cy3 image of a slide washed according to procedures described above with sodium borohydride and after arraying and hybridization obtained at a PMT setting of 950 volts. FIGS. 11A and 11B are graphs respectively showing the Cy3 RFU readings prior to hybridization and after hybridization. The image analysis results in FIG. 11A indicate that more than 80% of the autofluorescence on the GAPS surface was reduced after sodium borohydride treatment. FIG. 11B shows that excellent array and hybridization image was achieved with the slide treated with sodium borohydride. Even thought FIG. 11B shows that an equivalent amount of hybridization signal was obtained on both the sodium borohydride-treated and slides washed without sodium borohydride, higher signal-to-background ratio observed on sodium-borohydride-treated slide due to the significant reduction of surface auto-fluorescence.

It will be apparent to those skilled in the art that various modifications and variations can be made to the present invention without departing from the spirit or scope of the invention. For example, a variety of substrates containing various functional groups for noncovalent attachment to various biomolecules may be used in accordance with the present invention. Thus, it is intended that the present invention cover modifications and variations of this invention provided they come within the scope of the appended claims and their equivalents.

What is claimed is:

1. A method of eliminating autofluorescence from a substrate coated with a silane comprising treating at least a portion of a first surface of the substrate with a reducing agent.

2. The method of claim 1, wherein the silane coating includes an amino-silane.

3. The method of claim 1, wherein the silane coating includes gamma-amino-propyl-silane.

4. The method of claim 1, wherein the reducing agent includes a hydride.

5. The method of claim 1, wherein the reducing agent includes sodium borohydride.

6. The method of claim 5, wherein the sodium borohydride is in a solution at a concentration ranging from 0.01% to 1% by volume.

7. The method of claim 5, wherein the sodium borohydride is in a solution at a concentration ranging from 0.2% to 0.3% by volume.

8. The method of claim 1, wherein the reducing agent includes sodium cyanoborohydride.

9. The method of claim 1, wherein the reducing agent includes copper sulfate.

10. The method of claim 1, wherein the reducing agent includes hydrogen.

11. The method of claim 1, wherein the substrate is an inorganic material.

12. The method of claim 11, wherein the inorganic material is a metal, a semiconductor material, a glass, or a ceramic material.

13. The method of claim 12, wherein the metal is gold, platinum, nickel, palladium, aluminum, chromium, steel, or gallium arsenide.

14. The method of claim 12, wherein the semiconductor material is silicon or germanium.

15. The method of claim 12, wherein the glass or ceramic material is quartz, glass, porcelain, alkaline earth aluminoborosilicate glass, or a mixed oxide.

16. The method of claim 1, wherein the substrate is an organic material.

17. The method of claim 16, wherein the organic material is a polyester, a polyvinylchloride, a polyvinylidene fluoride, a polytetrafluoroethylene, a polycarbonate, a polyamide, a poly(meth)acrylate, a polystyrene, or a polyethylene or ethylene/vinyl acetate copolymer.

18. The method of claim 1, wherein the substrate is a glass slide.

19. The method of claim 1, wherein prior to contacting the substrate with the reducing agent, covalently or non-covalently attaching an array of target biomolecule to the first surface of the substrate.

* * * * *